(12) United States Patent
Van et al.

(10) Patent No.: US 7,446,099 B2
(45) Date of Patent: Nov. 4, 2008

(54) COMPOSITIONS AND METHODS FOR BIODEGRADABLE POLYMER-PEPTIDE MEDIATED TRANSFECTION

(75) Inventors: Sang Van, San Diego, CA (US); Nitnara Viroonchatapan, Oceanside, CA (US); Shouping Ji, Oceanside, CA (US); Kenji Matsumoto, San Diego, CA (US); Lei Yu, Carlsbad, CA (US)

(73) Assignee: Nitto Denko Corporation, Osaka (JP)

( * ) Notice: Subject to any disclaimer, the term of this patent is extended or adjusted under 35 U.S.C. 154(b) by 802 days.

(21) Appl. No.: 10/789,589

(22) Filed: Feb. 27, 2004

(65) Prior Publication Data

US 2005/0191746 A1   Sep. 1, 2005

(51) Int. Cl.
*A01N 43/48* (2006.01)
(52) U.S. Cl. .................. 514/44; 530/323; 424/93.2
(58) Field of Classification Search ........................ None
See application file for complete search history.

(56) References Cited

U.S. PATENT DOCUMENTS

2004/0247680 A1   12/2004   Farokhzad et al.

FOREIGN PATENT DOCUMENTS

| WO | WO 02/20663    |   | 3/2002 |
|----|----------------|---|--------|
| WO | WO 03/078576   |   | 9/2003 |
| WO | WO-03/078576   | * | 9/2003 |
| WO | WO 2004/009774 |   | 1/2004 |
| WO | WO 2004/076557 |   | 9/2004 |
| WO | WO 2005/032597 |   | 4/2005 |

OTHER PUBLICATIONS

Kakizawa, 2001, Biomacromolecules, 2, 491-497.*
Terwilliger, et al., 1982, Biophys. J., 37, 353-361.*
Kakizawa, Biomolecules, 2001, 2, 491-497.*
Chirila, et al. "The Use of Synthetic Polymers for Delivery of Therapeutic Antisense Oligodeoxynucleotides," *Biomaterials*, vol. 23, pp. 321-342, 2002.
Lim, et al. "Biodegradable Polyester, Poly[α-(4-Aminobutyl)-$_L$-Glycolic Acid], as a Non-Toxic Gene Carrier," *Pharmaceutical Research*, vol. 17, No. 7, pp. 811-816, 2000.
Lynn, et al. "Accelerated Discovery of Synthetic Transfection Vectors: Parallel Synthesis and Screening of a Degradable Polymer Library," *J. Am. Chem. Soc.*, vol. 123, pp. 8155-8156, 2001.
Futaki, et al. "Stearylated Arginine-Rich Peptides: A New Class of Transfection Systems," *Bioconjugate Chemistry*, vol. 12, pp. 1005-1011, 2001.
Legendre, et al. "Dioleoylmelittin as a Novel Serum-Insensitive Reagent for Efficient Transfection of Mammalian Cells," *Bioconjugate Chemistry*, vol. 8, pp. 57-63, 1997.
Siprashvili, et al. "Gene Transfer via Reversible Plasmid Condensation with Cysteine-Flanked, Internally Spaced Arginine-Rich peptides," *Human Gene Therapy*, vol. 14, pp. 1225-1233, Sep. 1, 2003.
Tung, et al. "Arginine Containing Peptides as Delivery Vectors," *Advanced Drug Delivery Reviews*, vol. 55, pp. 281-294, 2003.

* cited by examiner

*Primary Examiner*—Andrew D Kosar
*Assistant Examiner*—Satyanarayana R Gudibande
(74) *Attorney, Agent, or Firm*—Knobbe, Martens, Olson & Bear, LLP (57) ABSTRACT

Complexes are disclosed which are a combination of a polynucleotide and a biodegradable polyacetal-peptide. The disclosed complexes are useful for cell transfection.

16 Claims, 6 Drawing Sheets

Amino Acid Sequence (Peptide)

NH$_2$-GIGAVLKVLTTGLPALISWIKRKRQQ-COOH (Melittin) (SEQ ID NO: 1)

NH$_2$-CIGAVLKVLTTGLPALISWIKRKRQQ-COOH (Melittin-SH) (SEQ ID NO: 2)

NH$_2$-GIGAVLKVLTTGLPALISWIRRRRRRRQQ-COOH (NVG) (SEQ ID NO: 3)

NH$_2$-CIGAVLKVLTTGLPALISWIRRRRRRRQQ-COOH (NVC) (SEQ ID NO: 4)

NH$_2$-KRKRQQ-COOH (Mel-head-QQ) (SEQ ID NO: 5)

NH$_2$-CKRKRQQ-COOH (Mel-head-QQ-Cys) (SEQ ID NO: 6)

NH$_2$-CKRKR-COOH (Mel-head) (SEQ ID NO: 7)

NH$_2$-HLVKGRG-COOH (GLP-(1-6)-H) (SEQ ID NO: 8)

NH$_2$-CDCRGDCFC-COOH (RGD) (SEQ ID NO: 9)

NH$_2$-RRRRRRR-COOH (R7) (SEQ ID NO: 10)

NH$_2$-RRRR-COOH (R4) (SEQ ID NO: 11)

Poly(ethylenimine)-600    Polyacetal-GLP-(1-6)-H    Lipofectamine 2000

COMPOSITIONS AND METHODS FOR BIODEGRADABLE POLYMER-PEPTIDE MEDIATED TRANSFECTION

BACKGROUND OF THE INVENTION

1. Field of the Invention

This invention relates generally to delivery of biomolecules using biodegradable polymer-peptides. More particularly, this invention relates to acid sensitive biodegradable polyacetal conjugating peptides complexed with polynucleotides, methods for making the complexes, and methods for using them in polynucleotide delivery applications.

2. Description of the Related Art

There is a need for non-viral drug delivery systems having desirable properties such as low immunogenicity, amenable to production on a relatively large scale, and which can be easily modified to provide a range of biological properties. See Mulligan, R. C., "The basic science of gene therapy," Science 260, 926-932 (1993); and Luo, D. & Saltzman, W. M. "Synthetic DNA delivery systems," Nat. Biotechnol. 18, 33-37 (2000). However, non-degradable cationic polymers such as poly(lysine) and polyethyleneimine (PEI) can have significant cytotoxicity. See Choksakulnimitr, S., Masuda, S., Tokuda, H., Takakura, Y. & Hashida, M., "In vitro cytotoxicity of macromolecules in different cell culture systems," J. Control Release 34, 233-241 (1995); Brazeau, G. A., Attia, S., Poxon, S. & Hughes, J. A., "In Vitro Myotoxicity of Selected cationic macromolecules used in non-viral gene therapy," Pharm. Res. 15, 680-684 (1998); and Ahn, C.-H., Chae, S. Y., Bae, Y. H. & Kim, S. W. "Biodegradable poly(ethylenimine) for plasmid DNA delivery," J. Control. Release 80, 273-282 (2002).

To reduce cytotoxicity, some efforts have been made to develop degradable cationic polymers (polycations). See Ahn, C.-H., Chae, S. Y., Bae, Y. H. & Kim, S. W., "Biodegradable poly(ethylenimine) for plasmid DNA delivery," J. Control. Release 80, 273-282 (2002); Lynn, D. M.; Anderson, D. G.; Putman, D.; Langer, R., "Accelerated Discovery of Synthetic Transfection Vectors: Parallel Synthesis and Screening of a Degradable Polymer Library," J. Am. Chem. Soc. 123, 8155-8156 (2001); Lim, Y. et al., "Biodegradable Polyester, Poly[α-(4-Aminobutyl)-1-Glycolic Acid], as a Non-toxic Gene Carrier," Pharmaceutical Research 17, 811-816 (2000); Lim, Y., Kim, S., Suh, H. & Park, J.-S., "Biodegradable, Endosome Disruptive, and Cationic Network-type Polymer as a High Efficient and Non-toxic Gene Delivery Carrier," Bioconjugate Chem. 13, 952-957 (2002); Lim, Y. K., S.; Lee, Y.; Lee, W.; Yang, T.; Lee, M.; Suh, H.; Park, J., "Cationic Hyperbranched Poly(amino ester): A Novel Class of DNA Condensing Molecule with Cationic Surface, Biodegradable Three-Dimensional Structure, and Tertiary Amine Groups in the Interior," J. Am. Chem. Soc. 123, 2460-2461 (2001); and Tuominen, J. et al., "Biodegradation of Lactic Acid Based Polymers under Controlled Composting Conditions and Evaluation of the Ecotoxicological Impact," Biomacromolecules 3, 445-455 (2002). However, under physiological conditions, these cationic polymers are susceptible to degradation via base-catalyzed hydrolysis.

Acid-sensitive polymers containing acetal linkages has been reported, see Tomlinson, R. et al., "Pendent Chain Functionalized Polyacetals That Display pH-Dependent Degradation: A Platform for the Development of Novel Polymer Therapeutics," Macromolecules 35, 473-480 (2002); and Murthy, N., Thng, Y. X., Schuck, S., Xu, M. C. & Fréchet, J. M. J., "A Novel Strategy for Encapsulation and Release of Proteins: Hydrogels and Microgels with Acid-Labile Acetal Cross-Linkers," J. Am. Chem. Soc. 124, 12398-12399 (2002).

Using peptides for delivery of proteins has attracted a great deal of attention in the life science research area. Due to their natural properties, peptides were believed to be biocompatible. See Schwarze, S. R.; Ho, A.; Vocero-Akbani, A.; Dowdy, S. "In Vivo Protein Transduction: Delivery of a Biologically Active Protein into the Mouse." Science 285, 1560-1572 (1999), and Tung, C.; Weissleder, R. "Arginine containing peptides as delivery vectors." Adv. Drug Deliv. Rev. 55, 281-294 (2003). Recently, the utility of peptides as enhancers of gene delivery was reported. See Hawley-Nelson, P.; Lan, J.; Shih, P.; Jessee, J. A.; Schifferli, K. P.; Gebeyehu, G.; Ciccarone, V. C.; Evans, K. L. "Peptide-enhanced transfections." US Patent Application, US20030069173A1 (2003), and Hawley-Nelson, P.; Lan, J.; Shih, P.; Jessee, J. A.; Schifferli, K. P.; Gebeyehu, G.; Ciccarone, V. C.; Evans, K. L. "Peptide-enhanced transfections." US Patent Application, US20030144230A1 (2003). Peptide-mediated transfection also reported. See Legendre, J. Y.; Trzeiak, A.; Bohrmann, B.; Deuschle, U.; Kitas, E.; Supersaxo, A. "Dioleoylmelittin as a Novel Serum-Insensitive Reagent for Efficient Transfection of Mammalian Cells." Bioconjugate Chem. 8, 57-63 (1997), Futaki, S.; Ohashi, W.; Suzuki, T.; Niwa, M.; Tanaka, S.; Ueda, K.; Harashima, H.; Sugiura, Y. "Stearylated Arginine-Rich Peptides: A New Class of Transfection Systems." Bioconjugate Chem. 12, 1005-1011 (2001), Siprashvili, Z.; Scholl, F. A.; Oliver, S. F.; Adams, A.; Contag, C. H.; Wender, P. A.; Khavari, P. A. "Gene Transfer via Reversible Plasmid Condensation with Cysteine-Flanked, Internally Spaced Arginine-Rich Peptides." Human Gene Ther. 14, 1225-1233 (2003), Haines, A. M.; Phillips, R. O.; Welsh, J. H.; Thatcher, D. R.; Irvine, A. S. "Compositions and Methods for highly Efficient Transfection." PCT International Application, WO9835984 (1998), Haines, A. M.; Phillips, R. O.; Welsh, J. H.; Thatcher, D. R.; Irvine, A. S.; Craig, R. K. "Compositions and Methods for highly Efficient Transfection." U.S. Pat. No. 6,479,464B1 (2002), Haines, A. M.; Phillips, R. O.; Welsh, J. H.; Thatcher, D. R.; Irvine, A. S.; Craig, R. K. "Compositions and Methods for highly Efficient Transfection." US Patent Application, US20030100496 (2003), Divida, G.; Morris, M.; Mery, J.; Heitz, F.; Fernandez, J.; Archdeacon, J.; Horndorp, K. "Peptide-Mediated Delivery of Molecules into cells." PCT International Application, WO0210201A2 (2002), Divida, G.; Morris, M.; Mery, J.; Heitz, F.; Fernandez, J.; Archdeacon, J.; Horndorp, K. "Peptide-Mediated Transfection Agents and Methods of Use." US Patent Application, US20030119725A1 (2003), Wolff, J. A. "Compositions and Methods for Drug Delivery Using pH sensitive Molecules." PCT International Application. WO0075164A1 (2000), Phillips, R. O.; Welsh, J. H.; Husain, R. D. "Membrane disruptive peptides covalently oligomerized." PCT International Application. WO0064929 (2000), Legendre, J.; Supersaxo, A.; Trzeciak, A. "Peptide Conjugates for Transfecting Cells." U.S. Pat. No. 6,030,602 (2000), Wadwha, M. S.; Rolland, A.; Logan, M.; Sparro, J. T. "Lipophilic and/or lytic peptides for specific delivery of nucleic acids to cells." PCT International Application, WO9850078 (2000).

However, small peptides such as octaarginine without a tethered lipid chain are not particularly good for transfection. See Futaki, S.; Ohashi, W.; Suzuki, T.; Niwa, M.; Tanaka, S.; Ueda, K.; Harashima, H.; Sugiura, Y. "Stearylated Arginine-Rich Peptides: A New Class of Transfection Systems." 12, 1005-1011 (2001), and Tung, C.; Weissleder, R. "Arginine containing peptides as delivery vectors." Adv. Drug Deliv. Rev. 55, 281-294 (2003).

SUMMARY OF THE INVENTION

In some embodiments the invention is directed to a complex for delivering a polynucleotide to a cell, which includes: (a) a polynucleotide and (b) a biodegradable polyacetal-peptide. Preferably, the polynucleotide is DNA or RNA. More preferably, the polynucleotide is plasmid DNA, antisense, DNA oligomers, siRNA, ribozyme, or aptamer.

In preferred embodiments, the peptide comprises 2 to 45 amino acids with at least one or more arginine or lysine amino acids from 20 biological amino acids.

Figure 4:
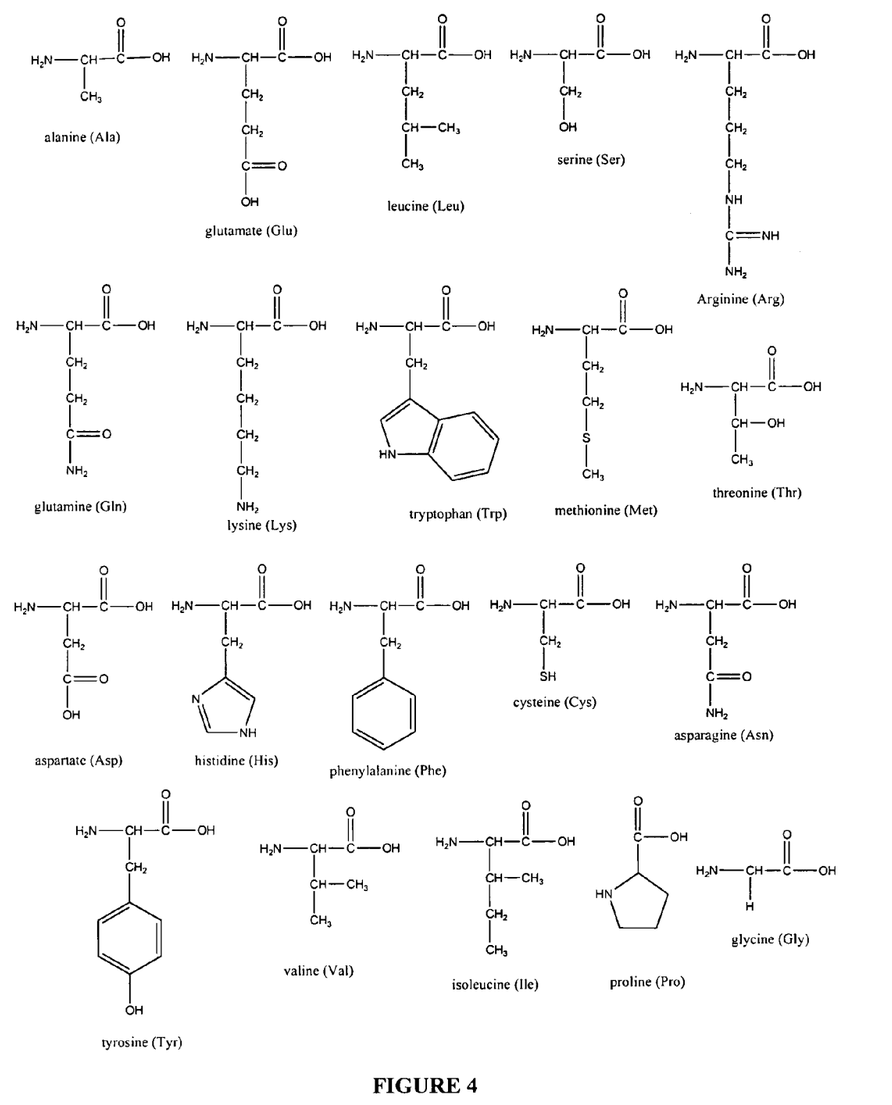
FIG. 4 shows structures of 20 biological amino acids.

Preferably, the biodegradable polyacetal-peptide includes at least one recurring unit represented by Formula (I) and/or (II):

(I)

wherein the peptide is selected from any continuous combination of 2 to 45 amino acids with at least one or more arginine or lysine amino acids from 20 biological amino acids (FIG. 4); X is selected from $CH_2CH_2$, $CH_2CH_2CH_2CH_2$, $CH_2CH_2OCH_2CH_2$, and $CH_2CH_2OCH_2CH_2OCH_2CH_2$; and Y is selected from linear or branched $C_4H_8$, $C_5H_{10}$, $C_6H_{12}$, $C_7H_{14}$, $C_8H_{16}$, $C_{10}H_{20}$, and $C_{12}H_{24}$. Yet more preferably, the peptide is selected from:

NH$_2$-GIGAVLKVLTTGLPALISWIKRKRQQ-COOH (SEQ ID NO: 1),

NH$_2$-CIGAVLKVLTTGLPALISWIKRKRQQ-COOH (SEQ ID NO: 2),

NH$_2$-GIGAVLKVLTTGLPALISWIRRRRRRRQQ-COOH (SEQ ID NO: 3),

NH$_2$-CIGAVLKVLTTGLPALISWIRRRRRRRQQ-COOH (SEQ ID NO: 4), NH$_2$-KRKRQQ-COOH (SEQ ID NO: 5),

NH$_2$-CKRKRQQ-COOH (SEQ ID NO: 6), NH$_2$-CKRKR-COOH (SEQ ID NO: 7), NH$_2$-HLVKGRG-COOH (SEQ ID NO: 8),

NH$_2$-CDCRGDCFC-COOH (SEQ ID NO: 9), NH$_2$-RRRR-COOH (SEQ ID NO: 11), or NH$_2$-RRRRRRR-COOH (SEQ ID NO: 10).

Preferably, X is selected from $CH_2CH_2$, $CH_2CH_2CH_2CH_2$, $CH_2CH_2OCH_2CH_2$, and $CH_2CH_2OCH_2CH_2OCH_2CH_2$; Y is selected from linear or branched $C_4H_8$, $C_5H_{10}$, $C_6H_{12}$, $C_7H_{14}$, $C_8H_{16}$, $C_{10}H_{20}$, and $C_{12}H_{24}$.

Preferably, the biodegradable polyacetal-peptide includes at least one recurring unit represented by Formula (III) and/or (IV):

(III)

(IV)

(II)

wherein, the peptide is any continuous combination of 2 to 45 amino acids with at least one or more arginine or lysine amino acids from 20 biological amino acids; X is $CH_2CH_2$, $CH_2CH_2CH_2CH_2$, $CH_2CH_2OCH_2CH_2$, or $CH_2CH_2OCH_2CH_2OCH_2CH_2$; Y is selected from linear or branched $C_4H_8$, $C_5H_{10}$, $C_6H_{12}$, $C_7H_{14}$, $C_8H_{16}$, $C_{10}H_{20}$, and $C_{12}H_{24}$; W is a fatty acid moiety or a targeting ligand selected from galactose, lactose, mannose, transferrin, antibody fragment, and RGD peptide; and m and n are positive integers.

In other embodiments, the invention is directed to a method of making the complex for delivering a polynucleotide to a cell which includes the step of intermixing the polyacetal-peptide and the polynucleotide.

In some embodiments, the invention is directed to a method for transfecting a cell, which includes contacting the cell with the polynucleotide-polyacetal-peptide complex.

In some embodiments, the invention is directed to the polyacetal-peptide represented by formula (I) or (II).

In some embodiments, the invention is directed to a method of cell transfection which includes the steps of:
(a) seeding cells to be transfected onto a solid support;
(b) mixing a polynucleotide for transfection with a polyacetal peptide;
(c) contacting the polynucleotide-polyacetal-peptide mixture with the seeded cells on the solid support; and
(d) incubating the solid support to allow transfection.

Preferably, the weight ratio of the polynucleotide to the polyacetal peptide is between about 1:4 and 1:50. More preferably, the weight ratio of the polynucleotide to the polyacetal peptide is between about 1:16 and 1:32.

In preferred embodiments, the method includes a polyacetal peptide which has at least one recurring unit represented by Formula (I) and/or (II):

(I)

(II)

wherein the peptide is any continuous combination of 2 to 45 amino acids with at least one or more arginine or lysine amino acids from 20 biological amino acids; X is $CH_2CH_2$, $CH_2CH_2CH_2CH_2$, $CH_2CH_2OCH_2CH_2$, or $CH_2CH_2OCH_2CH_2OCH_2CH_2$; and Y is linear or branched $C_4H_8$, $C_5H_{10}$, $C_6H_{12}$, $C_7H_{14}$, $C_8H_{16}$, $C_{10}H_{20}$, and $C_{12}H_{24}$.

In preferred embodiments, the method includes a polyacetal-peptide which has at least one recurring unit represented by Formula (III) and/or (IV):

wherein the peptide is any continuous combination of 2 to 45 amino acids with at least one or more arginine or lysine from 20 biological amino acids; X is $CH_2CH_2$, $CH_2CH_2CH_2CH_2$, $CH_2CH_2OCH_2CH_2$, or $CH_2CH_2OCH_2CH_2OCH_2CH_2$; Y is linear or branched $C_4H_8$, $C_5H_{10}$, $C_6H_{12}$, $C_7H_{14}$, $C_8H_{16}$, $C_{10}H_{20}$, and $C_{12}H_{24}$; W is a fatty acid moiety or a targeting ligand selected from galactose, lactose, mannose, transferrin, antibody fragment, and RGD peptide; and m and n are positive integers.

In preferred embodiments, the method includes a solid support which is a multiwell plate, a dish, a flask, a tube, a slide or an implanted device.

In preferred embodiments of the method, the polynucleotide is DNA, RNA, DNA/RNA hybrids or chemically modified nucleic acids. Preferably, the RNA is single-stranded or double-stranded. Preferably, the RNA is ribozyme or siRNA. In preferred embodiments, the DNA is circular, linear or single-strand oligonucleotide.

In preferred embodiment, the cells are prokaryotic or eukaryotic cells. Preferably, the eukaryotic cells are yeast, plant or animal cells. More preferably, the animal cells are mammalian cells. Yet more preferably, the mammalian cells are hematopoietic cells, neuronal cells, pancreatic cells, hepatic cells, chondrocytes, osteocytes, or myocytes. Yet more preferably, the neuronal cells are NT-2 cells. Preferably, the cells are fully differentiated cells or progenitor/stem cells.

Further aspects, features and advantages of this invention will become apparent from the detailed description of the preferred embodiments which follow.

BRIEF DESCRIPTION OF THE DRAWINGS

These and other feature of this invention will now be described with reference to the drawings of preferred embodiments which are intended to illustrate and not to limit the invention.

(III)

(IV)

DETAILED DESCRIPTION OF THE PREFERRED EMBODIMENT

In preferred embodiments, the present invention relates to the conjugation of small peptides to a biodegradable polymer. The polymer-peptide transfection reagents of the invention are biocompatible because of the nature of peptides. Thus, the invention will lead to in vivo delivery developments.

Preferred embodiments are directed to utilization of small peptides as effective transfection reagents. Preferably, the small peptides contain one or more amino acid residues that are positively charged at neutral pH. Small peptides are conjugated to biodegradable polymers to form biodegradable polymer-peptides. Preferred embodiments are directed to biodegradable polymer-peptides, compositions which include a complex of one or more polynucleotides along with a biodegradable polymer-polypeptide, methods of making the polynucleotide/polymer-polypeptide complexes, and methods of using the complexes in cell transfection. Preferred embodiments are directed to biodegradable polyacetal-peptides.

Polyacetals are polymers that contain acetal (—O—CHR—O—) recurring units. Preferred biodegradable polyacetal-peptides comprise recurring units represented by formula (I):

(I)

In preferred embodiments, the peptide of formula (I), is a linear or non-linear chain of 2-45 amino acid residues with at least one or more arginine or lysine amino acids. More preferably, the peptide is NH$_2$-GIGAVLKVLTTGLPAL-ISWIKRKRQQ-COOH (SEQ ID NO: 1), NH$_2$-CIGAVLKV-LTTGLPALISWIKRKRQQ-COOH (SEQ ID NO: 2), NH$_2$-GIGAVLKVLTTGLPALISWIRRRRRRRQQ-COOH (SEQ ID NO: 3), NH$_2$-CIGAVLKVLTTGLPALISWIR-RRRRRRQQ-COOH (SEQ ID NO: 4), NH$_2$-KRKRQQ-COOH (SEQ ID NO: 5), NH$_2$-CKRKRQQ-COOH (SEQ ID NO: 6), NH$_2$-CKRKR-COOH (SEQ ID NO: 7), NH$_2$-HLVKGRG-COOH (SEQ ID NO: 8), NH$_2$-CDCRGDCFC-COOH (SEQ ID NO: 9), NH$_2$-RRRR-COOH (SEQ ID NO: 11), or NH$_2$-RRRRRRRR-COOH (SEQ ID NO: 10).

In preferred embodiments, X is a linear or branched aliphatic chain of 2-15 carbons which may optionally include one or more, ether functional groups. More preferably, X includes any one of CH$_2$CH$_2$, CH$_2$CH$_2$CH$_2$CH$_2$, CH$_2$CH$_2$OCH$_2$CH$_2$, or CH$_2$CH$_2$OCH$_2$CH$_2$OCH$_2$CH$_2$.

Polyacetal-peptides may be copolymers and thus may contain two or more different recurring units represented by the formula (I) or other recurring units. Thus, the biodegradable polyacetal-peptide comprising recurring units represented by Formula (I) as this term is used herein includes such copolymers as well as homopolymers consisting essentially of recurring units of formula (I). In a preferred embodiment, the biodegradable polyacetal-peptide comprises a recurring unit of the formula (II):

(II)

In preferred embodiments, the peptide of formula (II) is a linear or non-linear chain of 2-45 amino acid residues with at least one or more arginine or lysine amino acids. More preferably, the peptide is NH$_2$-GIGAVLKVLTTGLPAL-ISWIKRKRQQ-COOH (SEQ ID NO: 1), NH$_2$-CIGAVLKV-LTTGLPALISWIKRKRQQ-COOH (SEQ ID NO: 2), NH$_2$-GIGAVLKVLTTGLPALISWIRRRRRRRQQ-COOH (SEQ ID NO: 3), NH$_2$-CIGAVLKVLTTGLPALISWIR-RRRRRRQQ-COOH (SEQ ID NO: 4), NH$_2$-KRKRQQ-COOH (SEQ ID NO: 5), NH$_2$-CKRKRQQ-COOH (SEQ ID NO: 6), NH$_2$-CKRKR-COOH (SEQ ID NO: 7), NH$_2$-HLVKGRG-COOH (SEQ ID NO: 8), NH$_2$-CDCRGDCFC-COOH (SEQ ID NO: 9), NH$_2$-RRRR-COOH (SEQ ID NO: 11), or NH$_2$-RRRRRRRR-COOH (SEQ ID NO: 10).

In preferred embodiments, X is a linear or branched aliphatic chain of 2-15 carbons which may optionally include one or more ether functional groups. More preferably, X includes any one of CH$_2$CH$_2$, CH$_2$CH$_2$CH$_2$CH$_2$, CH$_2$CH$_2$OCH$_2$CH$_2$, or CH$_2$CH$_2$OCH$_2$CH$_2$OCH$_2$CH$_2$.

In preferred embodiments, Y is a linear or branched aliphatic chain of 2 to 20 carbon atoms. More preferably, Y is selected from the group including linear or branched C$_4$H$_8$, C$_5$H$_{10}$, C$_6$H$_{12}$, C$_7$H$_{14}$, C$_8$H$_{16}$, C$_{10}$H$_{20}$, and C$_{12}$H$_{24}$.

In a preferred embodiment, the biodegradable polyacetal-peptide comprises a recurring unit of the formula (III):

(III)

In formula (III) above, the peptide may be from any continuous combination of 2 to 45 amino acids. In preferred embodiments, the peptide of formula (III) contains at least one or more arginine or lysine amino acids from 20 biological amino acids (FIG. 4). More preferably, the peptide is NH$_2$-GIGAVLKVLTTGLPALISWIKRKRQQ-COOH (SEQ ID NO: 1), NH$_2$-CIGAVLKVLTTGLPALISWIKRKRQQ-COOH (SEQ ID NO: 2), NH$_2$-GIGAVLKVLTTGLPALISWIRRRRRRQQ-COOH (SEQ ID NO: 3), NH$_2$-CIGAVLKVLTTGLPALISWIRRRRRRQQ-COOH (SEQ ID NO: 4), NH$_2$-KRKRQQ-COOH (SEQ ID NO: 5), NH$_2$-CKRKRQQ-COOH (SEQ ID NO: 6), NH$_2$-CKRKR-COOH (SEQ ID NO: 7), NH$_2$-HLVKGRG-COOH (SEQ ID NO: 8), NH$_2$-CDCRGDCFC-COOH (SEQ ID NO: 9), NH$_2$-RRRR-COOH (SEQ ID NO: 11), or NH$_2$-RRRRRRR-COOH (SEQ ID NO: 10).

In preferred embodiments, X is a linear or branched aliphatic chain of 2-15 carbons which may optionally include one or more ether functional groups. More preferably, X includes any one of $CH_2CH_2$, $CH_2CH_2CH_2CH_2$, $CH_2CH_2OCH_2CH_2$, and $CH_2CH_2OCH_2CH_2OCH_2CH_2$.

In preferred embodiments, W is an enhancer and/or a targeting receptor. More preferably, W is a fatty acid moiety or a targeting ligand selected from the group including galactose, lactose, mannose, transferrin, antibody fragment, and RGD peptide.

In preferred embodiments, m and n are integers from 1 to 50,000.

In a preferred embodiment, the biodegradable polyacetal-peptide comprises a recurring unit of the formula (IV):

(IV)

In formula (IV) above, the peptide may be from any continuous combination of 2 to 45 amino acids. In preferred embodiments, the peptide includes at least one or more arginine or lysine amino acids from 20 biological amino acids.

In preferred embodiments, X is a linear or branched aliphatic chain of 2-15 carbons which may optionally include one or more ether functional groups. More preferably, X includes any one of $CH_2CH_2$, $CH_2CH_2CH_2CH_2$, $CH_2CH_2OCH_2CH_2$, and $CH_2CH_2OCH_2CH_2OCH_2CH_2$.

In preferred embodiments, Y is a linear or branched aliphatic chain of 2 to 20 carbon atoms. More preferably, Y is selected from the group including linear or branched $C_4H_8$, $C_5H_{10}$, $C_6H_{12}$, $C_7H_{14}$, $C_8H_{16}$, $C_{10}H_{20}$, and $C_{12}H_{24}$.

In preferred embodiments, W is an enhancer and/or a targeting receptor. More preferably, W is a fatty acid moiety or a targeting ligand selected from the group including galactose, lactose, mannose, transferrin, antibody fragment, and RGD peptide.

Various methods may be used to make the polyacetal of the polyacetal peptide complex. Such methods are described for example in related application Ser. No. 10/375,705 which is incorporated herein by reference.

The concentration of polyacetal-peptide transfection reagent present in the mixture depends on the transfection efficiency and cytotoxicity of the reagent. Typically there is a balance between transfection efficiency and cytotoxicity. At concentrations in which the polymer-peptide transfection reagent is most efficient, while keeping cytotoxicity at an acceptable level, the concentration of polyacetal-peptide transfection reagent is at the optimal level. The concentration of polymer-peptide transfection reagent will generally be in the range of about 20 mg/mL to 1.0 mg/mL PBS.

The molecules to be introduced into cells can be nucleic acids, proteins, peptides, peptide nucleic acid (PNA) and other biomolecules. The nucleic acid can be DNA, RNA and DNA/hybrid, etc. If the DNA used is present in a vector, the vector can be of any type, such as a plasmid (e.g. example, pCMV-GFP, pCMV-luc) or viral-based vector (e.g. pLXSN). The DNA can also be linear fragment with a promoter sequence (such CMV promoter) at the 5' end of the cDNA to be expressed and a poly A site at the 3' end. These gene expression elements allow the cDNA of interest to be transiently expressed in mammalian cells. If the DNA is the single strand oligodeoxynucleotide (ODN), for example antisense ODN, it can be introduced into cells to regulate target gene expression. In embodiments using RNA the nucleic acid may be single stranded (antisense RNA and ribozyme) or double stranded (RNA interference, siRNA). In most cases, the RNA is modified in order to increase the stability of RNA and improve its function in down regulation of gene expression. In peptide nucleic acid (PNA), the nucleic acid backbone is replaced by peptide, which makes the molecule more stable. In particular embodiments the methods described herein can be used to introduce macromolecules such as nucleic acids into cells for various purposes, for example molecular therapy, protein function studies, or molecule mechanism studies.

The ratio of the molecule to be introduced and the polymer-peptide is preferably from about 1:4 to 1:50, more preferably from about 1:16 and 1:32.

Suitable cells for use according to the methods described herein include prokaryotes, yeast, or higher eukaryotic cells, including plant and animal cells, especially mammalian cells. In particular embodiments, the cells may be selected from hematopoietic cells, neuronal cells, pancreatic cells, hepatic cells, chondrocytes, osteocytes, or myocytes. The cells can be fully differentiated cells or progenitor/stem cells. In a preferred embodiment, the cells are neuronal cells, such as NT-2 cells. In a preferred embodiment, the transformed neuronal cells are used in a method of treating a neural disease such as Alzheimer or Parkinson disease.

In some embodiments, eukaryotic cells are grown in Dulbecco's Modified Eagles Medium (DMEM) containing 10% heat-inactivated fetal bovine serum (FBS) with L-glutamine and penicillin/streptomycin (pen/strep). It will be appreciated by those of skill in the art that certain cells should be cultured in a special medium, because some cells need special nutrition, such as growth factors and amino acids. The optimal density of cells depends on the cell types and the purpose of experiment. For example, a population of 70-80% confluent cells is preferred for gene transfection, but for oligonucleotide delivery the optimal condition is 30-50% confluent cells. For example, if $5 \times 10^4$ 293 cells/well were seeded onto a 96 well plate, the cells would reach 90% confluency at 18-24 hours after cell seeding. For HeLa 705 cells, only $1 \times 10^4$ cells/well are needed to reach a similar confluent percentage in a 96 well plate.

The results of biomolecule delivery can be analyzed by different methods. In the case of gene transfection and antisense nucleic acid delivery, the target gene expression level can be detected by reporter genes, such as green fluorescent protein (GFP) gene, luciferase gene, or β-galactosidase gene expression. The signal of GFP can be directly observed under a fluorescence microscope, the activity of luciferase can be detected by a luminometer, and the blue product catalyzed by β-galactosidase can be observed under microscope or determined by a microplate reader. One of skill in the art is familiar with how these reporters function and how they may be introduced into a gene delivery system. The nucleic acid and its product, the protein, peptide, or other biomolecules delivered according to methods described herein and the target modulated by these biomolecules can be determined by various methods, such as detecting immunofluorescence or enzyme immunocytochemistry, autoradiography, or in situ hybridization. If immunofluorescence is used to detect expression of an encoded protein, a fluorescently labeled antibody that binds the target protein is used (e.g., added to the slide under conditions suitable for binding of the antibody to the protein). Cells containing the protein are then identified by detecting a fluorescent signal. If the delivered molecules can modulate gene expression, the target gene expression level can also be determined by methods such as autoradiography, in situ hybridization, and in situ PCR. However, the identification method depends on the properties of the delivered biomolecules, their expression product, the target modulated by it, and/or the final product resulting from delivery of the biomolecules.

Example 1

Preparation of Materials Used in the Transfection Experiments

Cell lines and cultures used in the following examples were prepared as follows: Human embryonic carcinoma cells ("NT-2 cells") were grown in Dulbecco's-modified Eagle's medium (DMEM/F12, 90%) containing (v/v) heat-inactivated fetal bovine serum (FBS, 10%), 100 U/ml Penicillin and 100 μg/ml streptomycin, and incubated at 37° C. at 100% humidity atmosphere containing 7.5% $CO_2$.

GFP plasmids used in the following examples were prepared as follows: Plasmid pCMV-GFP and EGFP-$N_1$ were purchased from Clontech (Palo Alto, Calif.). The expression of green fluorescent protein (GFP) cDNA was controlled by human cytomegalovirus (CMV) promoter and the transcripts were stabilized by a gene expression enhancer, chicken β-globulin intron. The plasmid vector pCMV-luc was constructed by cloning the firefly luciferase gene into pCMV-0, with the same backbone of mammalian expression vector. The plasmid was expanded in DH5α E. Coli and purified with a Plasmid Maxi Kit (obtained commercially from Qiagen, Valencia, Calif.) according to the manufacturer's instructions.

Peptides were synthesized by the standard Fmoc procedure. Amino acid derivatives and resins were purchased from NovaBiochem, San Diego, Calif. All the other reagents and chemicals were purchased from Aldrich chemical Co. 1 (FIG. 2) was synthesized according to the procedure in U.S. provisional patent application No. 60/507,161, filed Sep. 29, 2003, which is incorporated herein by reference.

Example 2

Synthesis of Polyacetal

A solution of polyacetal 1 (1.5 g) in Dimethylformamide (DMF) (100 mL) was bubbled with argon gas for 3 minutes. 1,3-Dicyclohexylcarbodiimide (DCC, 2.7 g) and N-hydroxysuccinimide (NHS, 1.5 g) were added and continued to stir under argon atmosphere for 2 days. Precipitate formed and was filtered. The filtrate was concentrated by rotary evaporation. The residue was redissolved in dichloromethane (DCM, 50 mL) and any suspension was filtered. The filtrate was concentrated by rotary evaporation and placed under high vacuum to yield polyacetal 2 (1.7 g).

Example 3

Synthesis of Polyacetal-Peptides

Figure 2:
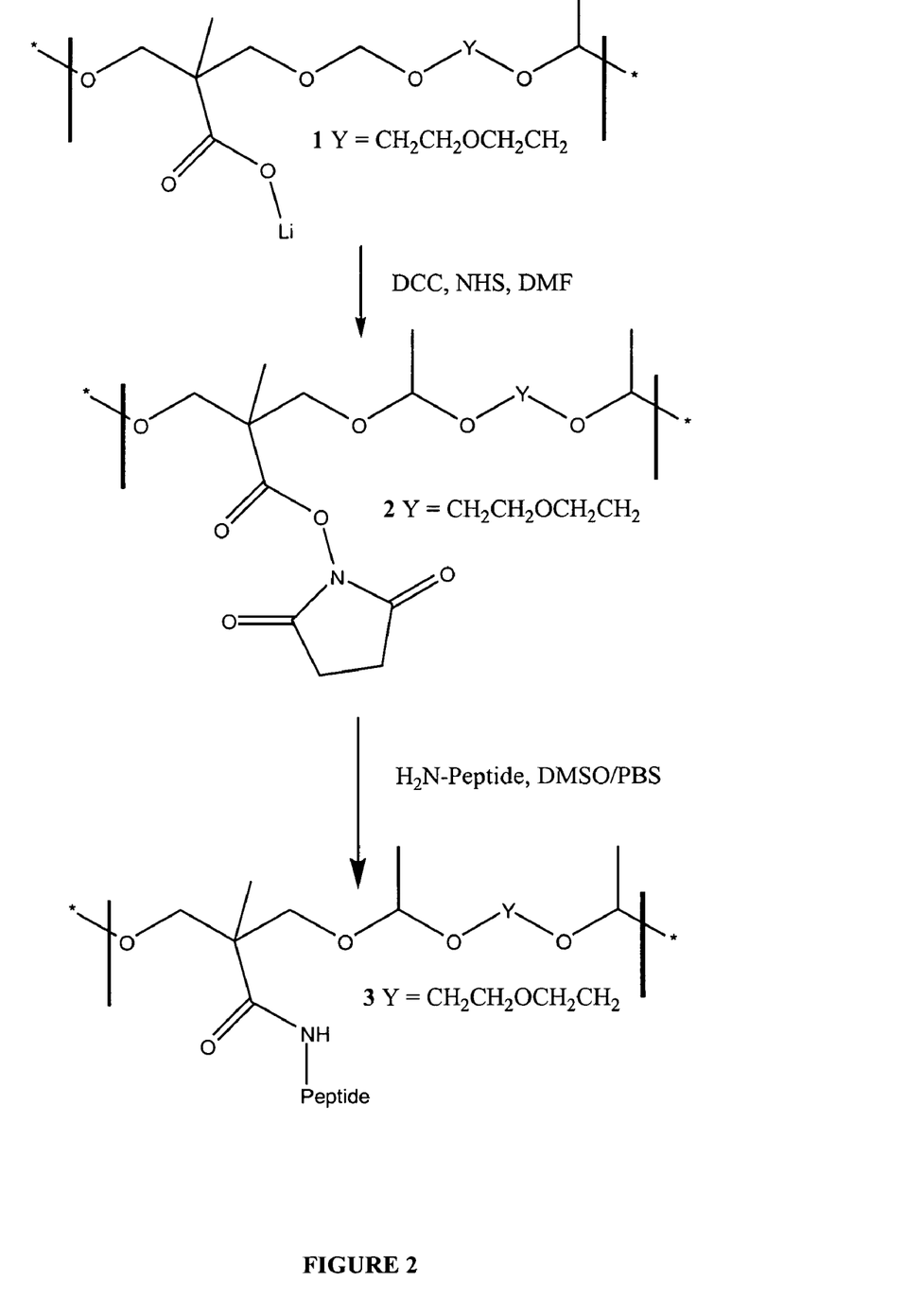
FIG. 2 shows a preferred reaction scheme for the preparation of polyacetal-peptides.

A solution of polyacetal 2 (10 mg) in dimethylsulfoxide (DMSO, 1 mL) was added to a solution of peptide (50 mg) in PBS (10 mL, adjusted to pH 7-8 with diluted NaOH solution). The mixture was stirred for 2 days, and then concentrated by rotary evaporation. The residue was dialyzed to yield polyacetal-peptides 3 (FIG. 2).

Example 4

Transfection of NT2 Cells with Polyacetal-Peptides

Figure 1:
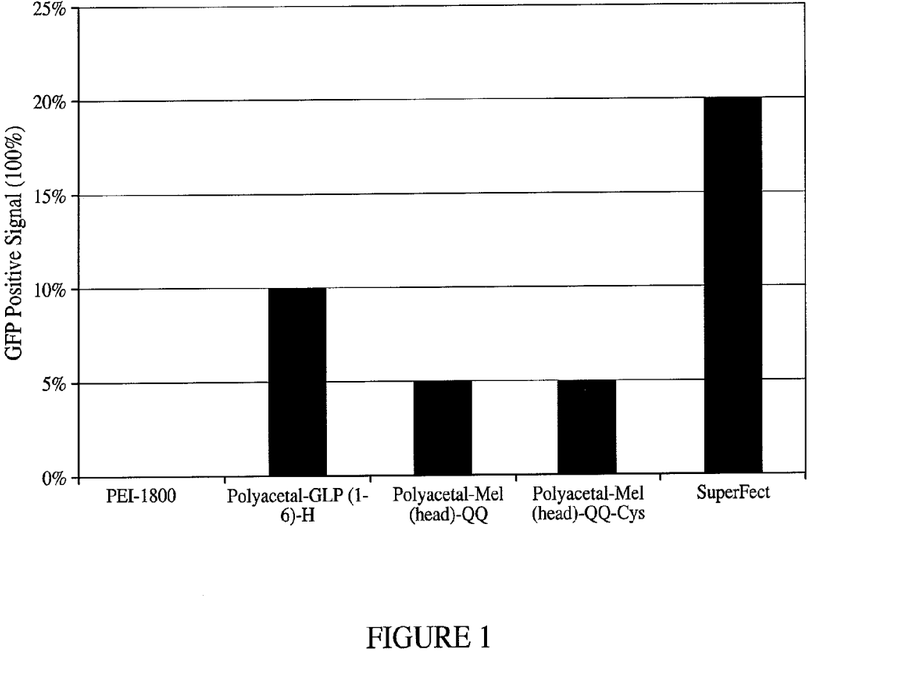
FIG. 1 shows a bar graph plotting GFP transfection signal (%) of NT-2 human embryonal carcinoma cells with plasmid DNA using polyacetal-peptides and a commercial reagent SuperFect (positive control). The results show that our polyacetal-peptides have transfected NT-2 cells. The ratio of polymer:DNA (by weight) is 32:1.
Figure 3:
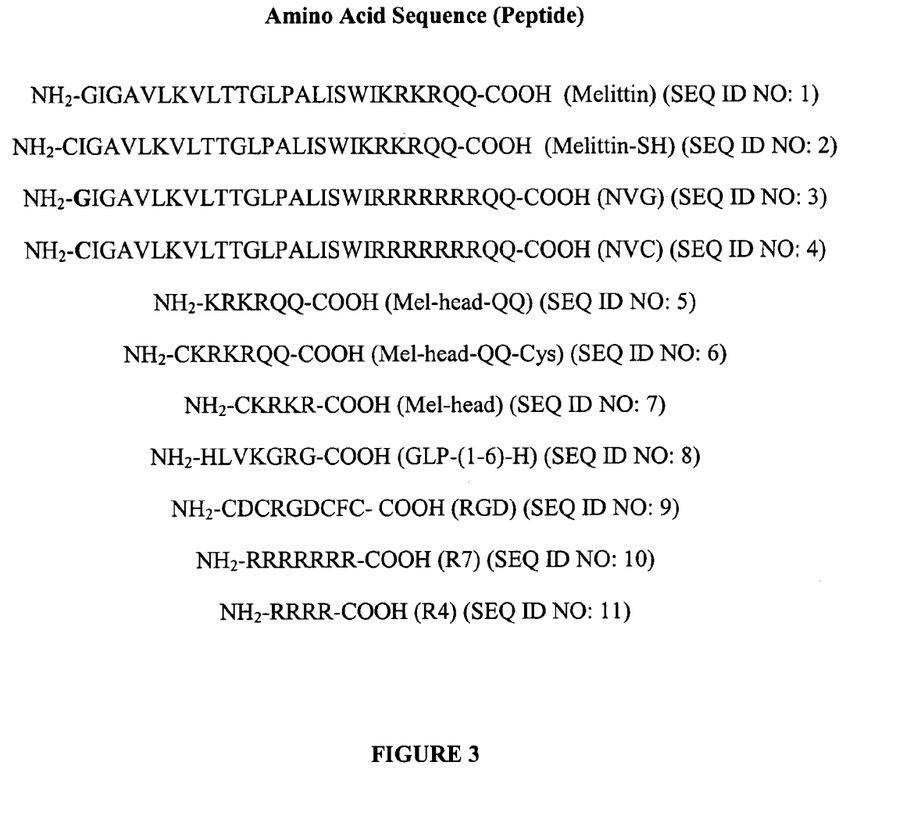
FIG. 3 shows preferred sequences of continuous amino acids of peptides.

Five polyacetal-peptide samples namely polyacetal-GLP-(1-6)-H, polyacetal-RGD, polyacetal-mel-head-QQ, polyacetal-mel-head-QQ-Cys, and polyacetal-mel-head were tested in NT2 cells (FIG. 3). Two polymer samples, PEI1800 and SuperFect, were used as negative and positive controls, respectively. The cells were seeded in a 96-well plate the night before an experiment at a cell density of $1\times10^4$ cells per well. On the day of the experiment, complexes of each sample and DNA were made at a sample:DNA ratio of 32:1. Fifteen microliters of each mixture were transferred to a NT2 cell culture plate, in duplicate. The culture plates were then kept overnight in the 37° C. incubator and the results were observed after 24 hours. As expected, the negative control did not show any transfection signal and the positive control showed about 15-20% of signal. Three of our polyacetal-peptides, where peptides are GLP-(1-6)-H, mel-head-QQ, and mel-head-QQ-Cys could disrupt the membrane and delivered the DNA plasmid into cells. The efficiency observed from our samples was about 5-10% which was fairly good (FIG. 1).

Example 5

Transfection of 293 Human Embryonic Kidney Cells with Polyacetal-Peptides

In vitro transfection using polyacetal-peptide was carried out as follows: 293 human embryonic kidney cells (adhesive common cells) were plated in 24-well tissue culture plates ($2\times10^5$ cells/well) and incubated overnight in DMEM with 10% fetal bovine serum (FBS). For each well, a 30 μl aliquot of polyacetal-peptide solution (each containing a different dose of polyacetal, ratios of polyacetal to polynucleotide of 32:1, by weight/weight) was added dropwise into a 30-μl DNA solution containing 0.6 μg of plasmid DNA, e.g. pCMV-EGFP plasmid DNA while vortexing. Dropwise addition while vortexing was found to be highly preferable, because it was found that transfection results depended on the mixing conditions. The mixed DNA and polyacetal-peptide solutions were incubated for 15 min at room temperature to form DNA-polyacetal-peptide complexes. Then 60 uL of DNA-polyacetal-peptide complex was added into each well and the cells were incubated (37° C., 7.5% $CO_2$) for 24 hours. After that incubation, GFP signals were detected as described below. Commercial transfection reagent Lipofectamine 2000 was used as a positive control according to the protocol provided by manufacturer and commercial transfection reagent polyethylenimine-600 daltons ($PEI_{600}$) was used as a negative control.

Example 6

GFP Observations Under Fluorescent Microscope

Figure 5:
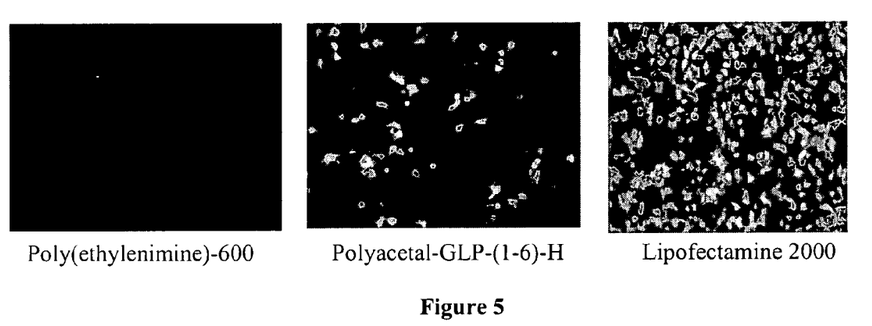
FIG. 5 shows transfection results of 293 cells based upon GFP signal with 3 different transfection agents: poly(ethylenimine)-600 (far left), polyacetal-GLP-(1-6)-H (center), and Lipofectamine 2000 (far right).

Green fluorescent signal in cells were observed under fluorescent microscope (Olympus, filter 520 nm). Cells were photographed using a 10× objective. The percent of cells with GFP signal in transfected cultures was determined from counts of three fields for optimal transfection agent amounts. The results obtained for the transfection of 293 cells with p-EGFP-$N_1$ using polyacetal-GLP-(1-6)-H, Lipofectamine 2000 (positive control) and PEI-1800 (negative control) are shown in FIG. 5. These results show that transfection efficiencies of polyacetal-peptide are much better compared with commercial agent poly(ethylenimine)-600 daltons.

Example 7

GFP Observations Under Microplate Fluorescence Reader

Figure 6:
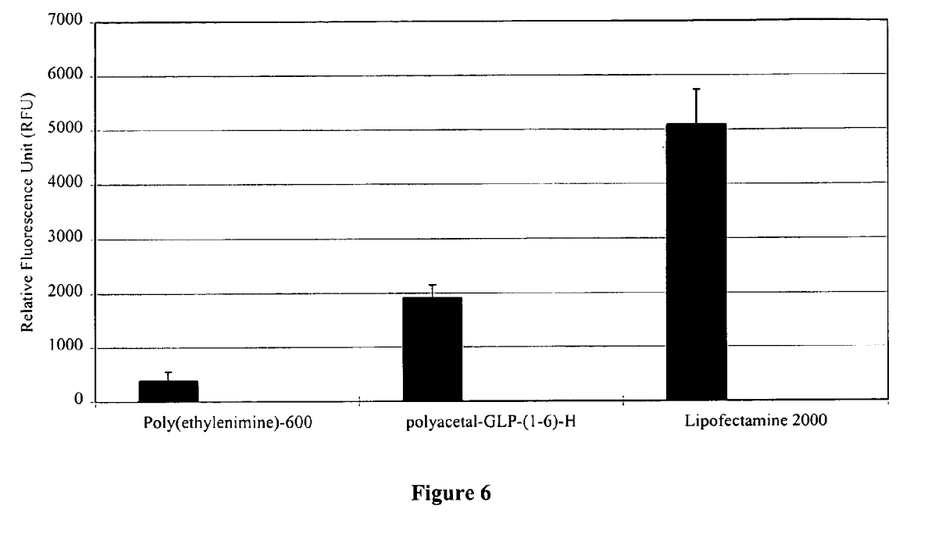
FIG. 6 shows relative fluorescent units for 293 cells transformed with poly(ethylenimine)-600, polyacetal-GLP-(1-6)-H, and Lipofectamine 2000.

Green fluorescent signal in cells were observed under microplate fluorescence reader (Model FLx800, Bio-Tek Instrument, Inc., filter with excitation at 485 nm and emission at 528 nm). GFP signal in transfected cultures was determined by the microplate fluorescence reader to give the relative fluorescence unit (RFU). The results obtained for the transfection of 293 cells with pCMV-EGFP using polyacetal-GLP-(1-6)-H, Lipofectamine 2000 (positive control) and PEI600 (negative control) are shown in FIG. 6 These results show that transfection efficiencies of polyacetal-peptide are much better compared with commercial agent poly(ethylenimine)-600 daltons.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A complex for delivering an isolated DNA to a cell, comprising: (a) the isolated DNA, and (b) a biodegradable polyacetal-peptide, wherein the biodegradable polyacetal-peptide comprises at least one recurring unit represented by a formula selected from the group consisting of (I) and (II):

wherein the peptide is selected from SEQ ID NOS: 5, 6 and 8;

wherein X is selected from the group consisting of $CH_2CH_2$, $CH_2CH_2CH_2CH_2$, $CH_2CH_2OCH_2CH_2$, and $CH_2CH_2OCH_2CH_2OCH_2CH_2$; and wherein Y is selected from the group consisting of linear or branched $C_4H_8$, $C_5H_{10}$, $C_6H_{12}$, $C_7H_{14}$, $C_8H_{16}$, $C_{10}H_{20}$, and $C_{12}H_{24}$.

2. The complex of claim 1 in which the DNA is selected from the group consisting of plasmid DNA and DNA oligomers.

3. A complex for delivering an isolated DNA to a cell, comprising: (a) the isolated DNA, and (b) a biodegradable polyacetal-peptide, wherein the biodegradable polyacetal-peptide comprises at least one recurring unit represented by a formula selected from the group consisting of (III) and (IV):

-continued (IV)

wherein the peptide is selected from SEQ ID NOS: 5, 6 and 8;

wherein X is selected from the group consisting of $CH_2CH_2$, $CH_2CH_2CH_2CH_2$, $CH_2CH_2OCH_2CH_2$, $CH_2CH_2OCH_2CH_2OCH_2CH_2$;

wherein Y is selected from the group consisting of linear or branched $C_4H_8$, $C_5H_{10}$, $C_6H_{12}$, $C_7H_{14}$, $C_8H_{16}$, $C_{10}H_{20}$, and $C_{12}H_{24}$, and wherein W is a fatty acid moiety or a targeting ligand selected from the group consisting of galactose, lactose, mannose, transferrin, antibody fragment, and RGD peptide; and m and n are positive integers.

4. A polyacetal-peptide represented by formula (I) or (II)

5. A method for transfecting an animal cell, comprising contacting the cell with the complex of claim 1.

6. A method of making a complex for delivering a polynucleotide to a cell comprising intermixing a solution comprising the polyacetal-peptide of claim 4 to a second solution comprising the DNA.

7. A method of animal cell transfection comprising the steps of: (a) seeding cells to be transfected onto a solid support;
   (b) contacting the complex of claim 1 with the seeded cells on the solid support; and
   (c) incubating the solid support to allow transfection.

8. The method of claim 7, wherein a weight ratio of the DNA to the polyacetal-peptide is between about 1:4 and 1:50.

9. The method of claim 8, wherein the weight ratio of the DNA to the polyacetal-peptide is between about 1:16 and 1:32.

10. The method of animal cell transfection comprising the steps of:
    (a) seeding cells to be transfected onto a solid support;
    (b) contacting the complex of claim 3 with the seeded cells on the solid support; and
    (c) incubating the solid support to allow transfection.

11. The method of claim 7, wherein the solid support is selected from the group consisting of a multiwell plate, a dish, a flask, a tube, a slide and an implantable device.

12. The method of claim 7, wherein the DNA is circular, linear or single-strand oligonucleotide.

13. The method of claim 7, wherein the animal cells are mammalian cells.

14. The method of claim 13, wherein the mammalian cells are selected from the group consisting of hematopoietic cells, neuronal cells, pancreatic cells, hepatic cells, chondrocytes, osteocytes, and myocytes.

15. The method of claim 14, wherein the neuronal cells are NT-2 cells.

16. The method of claim 7, wherein the cells are fully differentiated cells or progenitor/stem cells.

* * * * *

UNITED STATES PATENT AND TRADEMARK OFFICE
CERTIFICATE OF CORRECTION

| | |
|---|---|
| PATENT NO. | : 7,446,099 B2 |
| APPLICATION NO. | : 10/789589 |
| DATED | : November 4, 2008 |
| INVENTOR(S) | : Van et al. |

It is certified that error appears in the above-identified patent and that said Letters Patent is hereby corrected as shown below:

Title Page 1, Line 3, Item (75), "Shouping Ji, Oceanside, CA (US);" should be changed to --Shouping Ji, Vista, CA (US);--

Column 8, Line 8, "one or more ether," should be changed to --one or more ether--

Column 11, Line 47, "*E. Coli* and purified" should be changed to --*E. coli* and purified--

Column 14, Line 14, "PEI600 (negative control)" should be changed to --PEI-600 (negative control)--

Column 14, Line 14, "shown in FIG. 6" should be changed to --shown in FIG. 6.--

Signed and Sealed this

Fourteenth Day of April, 2009

JOHN DOLL
*Acting Director of the United States Patent and Trademark Office*

SEQUENCE LISTING

```
<160> NUMBER OF SEQ ID NOS: 11

<210> SEQ ID NO 1
<211> LENGTH: 26
<212> TYPE: PRT
<213> ORGANISM: Artificial Sequence
<220> FEATURE:
<223> OTHER INFORMATION: chemically synthesized peptide

<400> SEQUENCE: 1

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 2
<211> LENGTH: 26
<212> TYPE: PRT
<213> ORGANISM: Artificial Sequence
<220> FEATURE:
<223> OTHER INFORMATION: chemically synthesized peptide

<400> SEQUENCE: 2

Cys Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 3
<211> LENGTH: 29
<212> TYPE: PRT
<213> ORGANISM: Artificial Sequence
<220> FEATURE:
<223> OTHER INFORMATION: chemically synthesized peptide

<400> SEQUENCE: 3

Gly Ile Gly Ala Val Leu Lys Val Leu Thr Thr Gly Leu Pro Ala Leu
1               5                   10                  15
```

-continued

```
Ile Ser Trp Ile Arg Arg Arg Arg Arg Arg Gln Gln
            20                  25

<210> SEQ ID NO 4
<211> LENGTH: 29
<212> TYPE: PRT
<213> ORGANISM: Artificial Sequence
<220> FEATURE:
<223> OTHER INFORMATION: chemically synthesized peptide

<400> SEQUENCE: 4

Cys Ile Gly Ala Val Leu Lys Val Leu Thr Thr Gly Leu Pro Ala Leu
1               5                   10                  15

Ile Ser Trp Ile Arg Arg Arg Arg Arg Arg Gln Gln
            20                  25

<210> SEQ ID NO 5
<211> LENGTH: 6
<212> TYPE: PRT
<213> ORGANISM: Artificial Sequence
<220> FEATURE:
<223> OTHER INFORMATION: chemically synthesized peptide

<400> SEQUENCE: 5

Lys Arg Lys Arg Gln Gln
1               5

<210> SEQ ID NO 6
<211> LENGTH: 7
<212> TYPE: PRT
<213> ORGANISM: Artificial Sequence
<220> FEATURE:
<223> OTHER INFORMATION: chemically synthesized peptide

<400> SEQUENCE: 6

Cys Lys Arg Lys Arg Gln Gln
1               5

<210> SEQ ID NO 7
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 7

Cys Lys Arg Lys Arg
1               5

<210> SEQ ID NO 8
<211> LENGTH: 7
<212> TYPE: PRT
<213> ORGANISM: Artificial Sequence
<220> FEATURE:
<223> OTHER INFORMATION: chemically synthesized peptide

<400> SEQUENCE: 8

His Leu Val Lys Gly Arg Gly
1               5

<210> SEQ ID NO 9
<211> LENGTH: 9
<212> TYPE: PRT
<213> ORGANISM: Artificial Sequence
<220> FEATURE:
<223> OTHER INFORMATION: chemically synthesized peptide
```

-continued

```
<400> SEQUENCE: 9

Cys Asp Cys Arg Gly Asp Cys Phe Cys
1               5

<210> SEQ ID NO 10
<211> LENGTH: 7
<212> TYPE: PRT
<213> ORGANISM: Artificial Sequence
<220> FEATURE:
<223> OTHER INFORMATION: chemically synthesized peptide

<400> SEQUENCE: 10

Arg Arg Arg Arg Arg Arg Arg
1               5

<210> SEQ ID NO 11
<211> LENGTH: 4
<212> TYPE: PRT
<213> ORGANISM: Artificial Sequence
<220> FEATURE:
<223> OTHER INFORMATION: chemically synthesized peptide

<400> SEQUENCE: 11

Arg Arg Arg Arg
1
```